United States Patent
Ansari et al.

(10) Patent No.: US 10,942,165 B1
(45) Date of Patent: Mar. 9, 2021

(54) METHODS FOR PREPARING CARTRIDGES FOR IN VITRO DIAGNOSTICS AND RELATED SYSTEMS

(71) Applicant: DNAe Group Holdings Ltd, London (GB)

(72) Inventors: Zahid Ansari, Cambridge (GB); Peter Charles Howard, Bristol (GB); Francois Paillier, London (GB); Christopher Maurice Neville Tofts, Bristol (GB)

(73) Assignee: DNAe Group Holdings Ltd, London (GB)

( * ) Notice: Subject to any disclaimer, the term of this patent is extended or adjusted under 35 U.S.C. 154(b) by 0 days.

(21) Appl. No.: 16/722,888

(22) Filed: Dec. 20, 2019

(51) Int. Cl.
| | | |
|---|---|---|
| *G01N 33/49* | (2006.01) | |
| *G01N 33/53* | (2006.01) | |
| *G01N 33/52* | (2006.01) | |
| *B01L 3/00* | (2006.01) | |

(52) U.S. Cl.
CPC ...... *G01N 33/492* (2013.01); *B01L 3/502753* (2013.01); *B01L 3/502761* (2013.01); *G01N 33/526* (2013.01); *G01N 33/5306* (2013.01); *G01N 33/5308* (2013.01); *B01L 2200/0621* (2013.01); *B01L 2200/10* (2013.01); *B01L 2300/0816* (2013.01); *B01L 2300/0822* (2013.01); *B01L 2300/0867* (2013.01); *G01N 2496/80* (2013.01)

(58) Field of Classification Search
None
See application file for complete search history.

(56) References Cited

U.S. PATENT DOCUMENTS

2003/0152927 A1\* 8/2003 Jakobsen ............... G02B 21/34
435/6.16

\* cited by examiner

*Primary Examiner* — G Steven Vanni
(74) *Attorney, Agent, or Firm* — Vorys, Sater, Seymour and Pease LLP (57) ABSTRACT

A method for increasing the number of analyte/assay combinations in a single chip or cartridge of an in vitro diagnostic system may include: prioritizing a set of analyte/assay combinations based on characteristics of each analyte in the set of analyte/assay combinations, wherein the characteristics comprise one selected from the group consisting of a prevalence of each analyte, a clinical relevance of each analyte, a clinical actionability of each analyte, a patient benefit, a cost savings, and any combination thereof; deriving an analyte/analyte interactivity for two or more analytes in the set of analyte/assay combinations; designing a plurality of candidate panel layouts based on panel layout rules, the prioritization of the set of analyte/assay combinations, and the analyte/analyte interactivity, wherein the panel layout comprises one or more chips each comprising a chamber with two or more analytes; and validating the plurality of candidate panel layouts to produce panel layout solutions.

23 Claims, 3 Drawing Sheets

METHODS FOR PREPARING CARTRIDGES FOR IN VITRO DIAGNOSTICS AND RELATED SYSTEMS

BACKGROUND

The present application relates to in vitro diagnostic (IVD) systems.

IVD systems are used to identify clinically relevant analytes in a sample. Such analytes can be, for example, a DNA sequence, a gene, a protein, and the like. The detection of clinically relevant analytes can be carried out using disposable chips or assemblies of two or more chips referred to as a cartridge. Each disposable chip has several reaction chambers. Each reaction chamber is used for the detection of a single analyte. Detection of the analyte can be achieved by adding an assay (e.g., a probe or an antibody) specific to the analyte of interest to the chamber such that when the analyte is present a detectable change (e.g., activation or deactivation of a fluorescent molecule or a change in color) occurs within the chamber. Typically, each combination of analyte and assay is performed in triplicate to reduce error.

IVD systems and related methods can be used to screen hundreds of analyte/assay combinations, which makes this a powerful tool. In order to maximize the value of a panel (the analyte/assay combinations in one chip or cartridge), systems engineers try to maximize the number of assays that can be deployed in a chip or cartridge by maximizing the number of reaction chambers. However, the individual chambers have size limitations because a minimum volume of fluid is needed for each analyte/assay combination and detection systems have spatial limitations so that each reaction chamber is independently measured without interferences from an adjacent chamber. Accordingly, other ways to increase the number of assays in a single panel would be advantageous.

SUMMARY OF THE INVENTION

The present application relates to increasing the number of analyte/assay combinations in a single chip or cartridge of an IVD system by designing panel layouts with more than one analyte in some or all of the chambers of the chip or cartridge.

A nonlimiting example method for increasing the number of analyte/assay combinations in a single chip or cartridge of an IVD system comprises: prioritizing a set of analyte/assay combinations based on characteristics of each analyte in the set of analyte/assay combinations, wherein the characteristics comprise one selected from the group consisting of a prevalence of each analyte, a clinical relevance of each analyte, a clinical actionability of each analyte, a patient benefit, a cost savings, and any combination thereof; deriving an analyte/analyte interactivity for two or more analytes in the set of analyte/assay combinations; and designing a plurality of candidate panel layouts based on panel layout rules, the prioritization of the set of analyte/assay combinations, and the analyte/analyte interactivity, wherein the panel layout comprises one or more chips each comprising a chamber with two or more analytes; and validating the plurality of candidate panel layouts to produce one or more panel layout solutions.

A nonlimiting example system for increasing the number of analyte/assay combinations in a single chip or cartridge of an IVD system comprises: a processor; a non-transitory machine-readable medium that stores machine-readable instructions for execution by the processor, the machine-readable instructions comprising: prioritize a set of analyte/assay combinations based on characteristics of each analyte in the set of analyte/assay combinations, wherein the characteristics comprise one selected from the group consisting of a prevalence of each analyte, a clinical relevance of each analyte, a clinical actionability of each analyte, a patient benefit, a cost savings, and any combination thereof; derive an analyte/analyte interactivity for two or more analytes in the set of analyte/assay combinations; design a plurality of candidate panel layouts based on panel layout rules, the prioritization of the set of analyte/assay combinations, and the analyte/analyte interactivity, wherein the panel layout comprises one or more chips each comprising a chamber with two or more analytes; and validate the plurality of candidate panel layouts to produce one or more panel layout solutions.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The present application relates to increasing the number of analyte/assay combinations in a single chip or cartridge of an IVD system by designing panel layouts with more than one analyte in some or all of the chambers of the chip or cartridge.

The chip or cartridges may include semiconductor devices, plates (e.g., 96-well PCR plates), and other similar systems that are configured to have multiple chambers and are suitable for one or more of the detection methods described herein.

Figure 1:
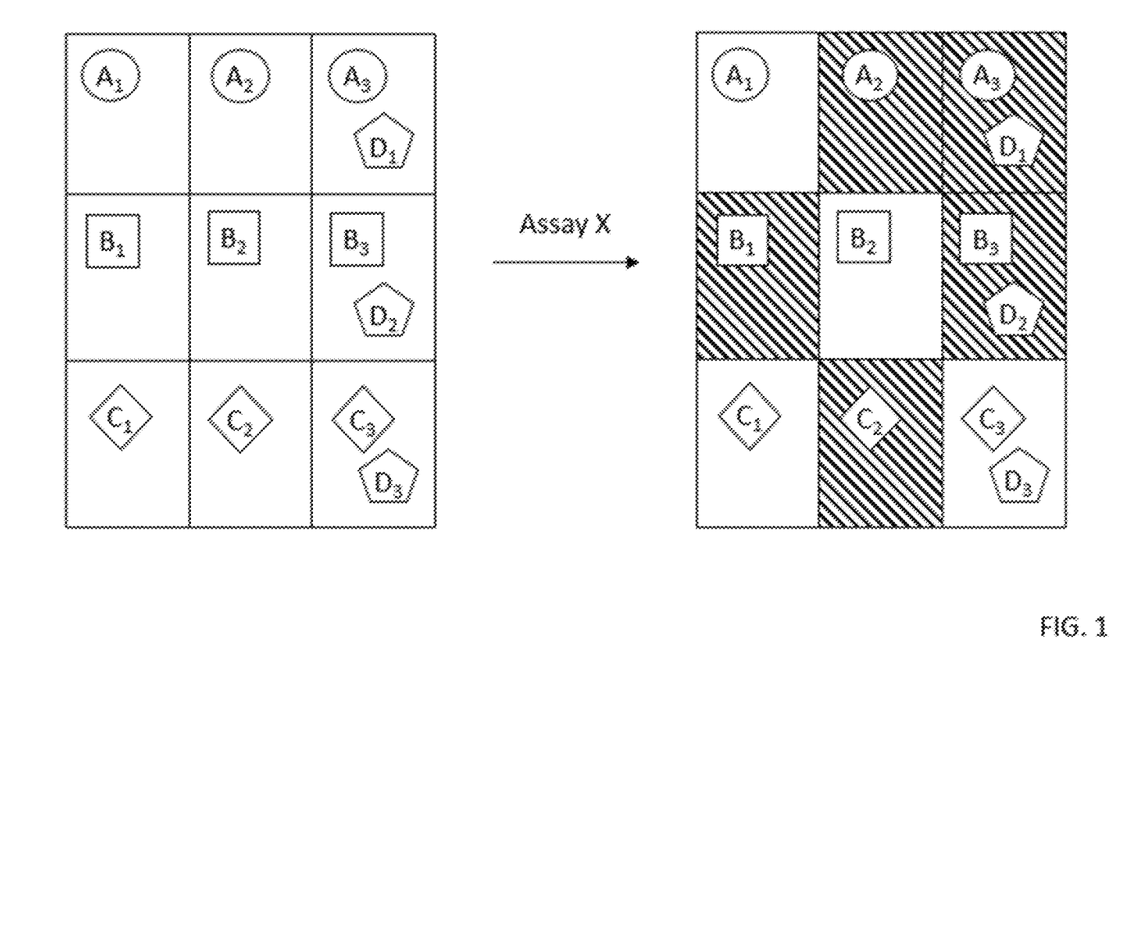
FIG. 1 illustrates a panel layout where analytes A, B, C, and D, are in triplicate and distributed in 9 chambers.

Including more than one analyte in a chamber makes distinguishing which analyte responded to the assay difficult to impossible. FIG. 1, for example, illustrates a panel layout where analytes A, B, C, and D are in triplicate and distributed in 9 chambers. More specifically, the first and second replicates of analytes A, B, and C are in individual chambers alone, and the third replicate of analytes A, B, and C each have a single replicate of analyte D also in the corresponding chamber. Assay X is added to each of the chambers. Upon interaction between an analyte and the assay, a detectible change in the chamber occurs, which is indicated in FIG. 1 by a diagonal pattern in the chamber. At least two out of three results being positive (diagonal pattern) or negative (no change) determines if the analyte does or does not interact, respectively, with the assay.

In this example, the chambers containing each of analytes A, B, and D each have two positive results and one negative result, and the chambers containing analyte C have two negative results and one positive result. However, because there are chambers with two analytes, the results are not that straightforward. Analyte C has one positive and one negative result in the two chambers where analyte C is alone. In the chamber having analyte C and D, the result is negative, which is considered a negative result for both analytes C and D. Therefore, analyte C has two definitive negative results and is determined to have no interaction with assay X.

The two chambers for each of analytes A and B have one positive result and one negative result. The chambers for the mixtures of analytes A and D and of analytes B and D have a positive result. However, because the chambers have two analytes it is unclear which analyte is interacting with assay X. If you assume analyte D and assay X do not interact, then the positive results in the mixed analyte chambers are due to the other analyte. Accordingly, both analytes A and B would be determined to have an interaction with assay X. However, if you assume analyte D and assay X do interact, then the interaction between each of analytes A and B with assay X are unknown and could be positive or negative, which means the results of this panel could be one of the five results in Table 1.

TABLE 1

| Possible Result | Assay X Interaction with | | | |
| --- | --- | --- | --- | --- |
| Number | Analyte A | Analyte B | Analyte C | Analyte D |
| 1 | Positive | Positive | Negative | Negative |
| 2 | Positive | Positive | Negative | Positive |
| 3 | Positive | Negative | Negative | Positive |
| 4 | Negative | Positive | Negative | Positive |
| 5 | Negative | Negative | Negative | Positive |

Therefore, simply adding two analytes to the same chamber creates ambiguous results.

The present disclosure provides an algorithmic approach to designing panel layouts to mitigate ambiguous results when at least some of the chambers include two or more analytes. When designing a complex panel layout with potentially tens to hundreds of chambers over one or more chips and/or cartridges and two or more analyte/assay combinations in most of the chambers, the number of possible panel layouts becomes tremendous. The algorithmic approach described herein improves the likelihood of designing and implementing a panel layout that results in data having a high degree of accuracy. This in combination with the fact that the two or more analyte/assay combinations chambers increases the throughput and lowers the cost of the panel results in a significant improvement to in vitro diagnostic technology.

Examples of analytes include, but are not limited to, genes, proteins, antibodies, bacteria, fungi, DNA, RNA, blood cells, platelets, lipids, nucleic acids, enzymes, hormones, cellular receptors, carbohydrates, and the like, and any combination thereof. Additional examples of analytes are infectious diseases from fungi, viruses, bacteria, and the like as well as the linked or corresponding anti-microbial resistant genes. Examples of such infectious diseases may include, but are not limited to, Lyme disease, cholera, meningitis, bacterial vaginosis, syphilis, tetanus, typhoid fever, Ebola, measles, chickenpox, herpes, human papillomavirus, influenza, polio, shingles, rubella, smallpox, rabies, yellow fever, athlete's foot, ringworm, candidiasis, and the like.

Suitable assays may be for the prevention, mitigation, and/or treatment of diseases, conditions, and/or symptoms thereof in a patient. Examples of diseases and conditions may include, but are not limited to, arthritis, rheumatoid arthritis, juvenile rheumatoid arthritis, psoriatic arthritis, osteoarthritis, gouty arthritis, refractory rheumatoid arthritis, chronic non-rheumatoid arthritis, osteoporosis/bone resorption, osteoporosis, ulcerative colitis, skin diseases, psoriasis, acne vulgaris, rosacea, dermatitis, contact dermatitis, eczema, delayed-type hypersensitivity in skin disorders, type I diabetes, type II diabetes, Alzheimer's disease, inflammatory disorders, immunodeficiency, inflammatory bowel disease, irritable bowel syndrome, Crohn's disease, diarrhea disease, antibiotic-associated diarrhea, pediatric diarrhea, chronic constipation, heartburn, appendicitis, autoimmune disorders, multiple sclerosis, muscle degeneration, coeliac disease, diabetes mellitus, organ transplantation, bacterial infectious diseases including the linked or corresponding anti-microbial resistant genes, viral infectious diseases including the linked or corresponding anti-microbial resistant genes, fungal infectious diseases including the linked or corresponding anti-microbial resistant genes, periodontal disease, urogenital disease, sexually transmitted diseases, HIV infection, HIV replication, HIV associated diarrhea, surgical associated trauma, surgical-induced metastatic disease, nausea, weight loss, weight gain, anorexia, bulimia, fever control, cachexia, wound healing, ulcers, gut barrier function, allergies, Hay Fever, allergic rhinitis, anaphylaxis, asthma, respiratory disorders, lung diseases, pulmonary fibrosis, chronic obstructive pulmonary disease, circulatory disorders, anemia, disorders of the blood coagulation system, renal disease, disorders of the central nervous system, hepatic disease, ischemia, nutritional disorders, endocrine disorders, epidermal disorders, multiple myeloma, uveitis, acute and chronic myelogenous leukemia, anti-clotting, coronary heart disease, vasculitis, ischemic heart disease, atherosclerosis, strokes, peripheral arterial disease, ischemic-induced cell damage, high blood cholesterol levels, high-density lipoprotein (HDL) levels, high blood pressure, pancreatic 13 cell destruction, rheumatoid spondylitis, adult respiratory distress syndrome (ARDS), bone resorption diseases, ischemia reperfusion injury, brain trauma, cerebral malaria, sepsis, septic shock, toxic shock syndrome, blood infection, fever, myalgias due to infection, HIV-1, HIV-2, HIV-3, immune system disorders, cytomegalovirus, colds, influenza, adenovirus, the herpes viruses (including HSV-1, HSV-2), herpes zoster infection, herpes simplex/cold sores, infections, disorders associated with C-reactive protein, myositis, lupus, Celiac disease, prostatitis, tumor, sexual dysfunction, inflammatory disease, thyroid diseases, pregnancy, headaches, acute pain, rashes, addiction, addiction to habit forming drugs, addiction to smoking, upper respiratory tract infection, neurodegenerative disease, dyslexia, dyspraxia, autism, Asperger's disease, mild cognitive impairment, poor concentration, attention deficit disorder (ADD), attention deficit hyperactive disorder (ADHD), depression, mood swings, bipolar disorders, cancer, leukemia, acute and chronic myelogenous leukemia, colon cancer, prostate cancer, kidney cancer, liver cancer, breast cancer, lung cancer, melanoma, brain cancer, cervical cancer, Hodgkin's lymphoma, non-Hodgkin's lymphoma, ovarian cancer, testicular cancer, thyroid cancer, uterine cancer, urinary tract infection, nervous system infection, and the like. The controlled release vehicles of the present invention may be useful in the prevention, mitigation, and/or treatment of other diseases, conditions, and/or symptoms.

Examples of assays include, but are not limited to, ion sensitive field effect transistor (ISFET), NAAT-based (nucleic acids amplification technologies) assays, antibody assays, active pharmaceuticals, prodrugs of active pharmaceuticals, active biologicals, antibiotics, antifungals, antitoxins, antigens, therapeutics, preventive therapeutics, nutritional supplements, imaging agents, fluid stabilizers, food agents, flavorants, olfactory agents, plant agents, chemical-reaction agents, and the like, and any combination thereof.

Figure 2:
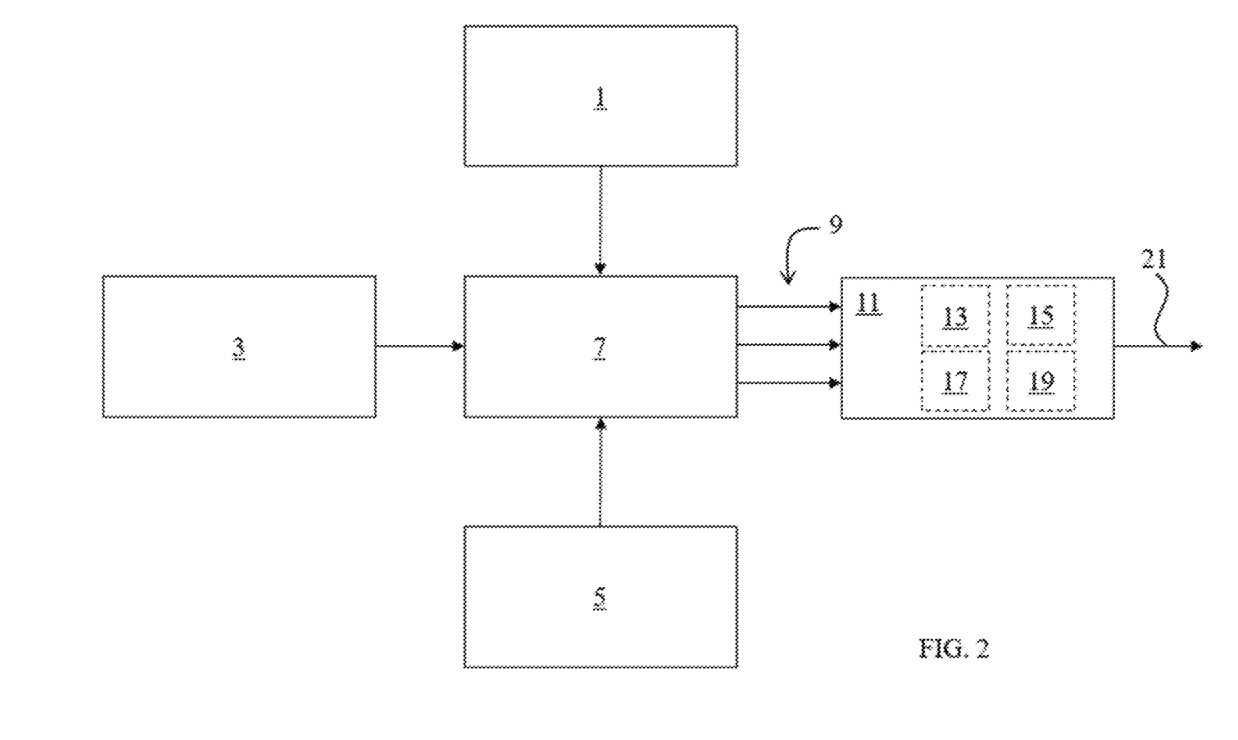
FIG. 2 illustrates an approach of the present disclosure for designing panel layouts.

FIG. 2 illustrates an approach of the present disclosure for designing panel layouts. The approach uses a first model 7 with inputs that include panel layout rules 1, a prioritization of a set of analyte/assay combinations 3, and an analyte/analyte interactivity 5 to produce a plurality of candidate panel layouts 9 based on the inputs 1, 3, 5. Then, a second model 11 validates the plurality of candidate panel layouts 9 to arrive at one or more panel layout solutions 21 that mitigate ambiguous results.

The panel layout rules 1 can include, but are not limited to, a number of replicates for each analyte/assay combination in the panel, a number of replicates for each analyte/assay combination per chip and/or cartridge, a number of replicates for each analyte/assay combination in total, a number of control chambers, a number of control chambers per chip and/or cartridge an amount of chambers in which two or more analyte/assay combinations can be paired, a number of analyte/assay combinations per chamber, and the like, and any combination thereof.

Increasing the number of replicates for each analyte/assay combination in the panel increases the robustness of the approach and mitigates ambiguity in the data. However, unnecessary replicates consume valuable chamber space. The number of replicates needed depends on analyte/assay combination and the number of analyte/assay combinations per chamber. Typically, the number of replicates for each analyte/assay combination per panel can be 2 to 5, or 3 to 4. The number of replicates for each analyte/assay combination per panel may be defined as a specific value, a maximum number, or a range.

As described previously, each panel can include one or more chip and/or cartridge. Preferably, multiple chips and/or cartridges are used. Further, where possible, each replicate of an analyte/assay combination is preferably on a different chip. This further strengthens the robustness of the present approach because if the data from a chip is not useable, not all data for the analyte/assay combination are lost. While this may introduce ambiguity into the results because fewer replicates of the analyte/assay combination are completed, the overall panel can still provide meaningful data. However, the number of replicates for each analyte/assay combination per chip and/or cartridge may be dependent on the analyte/assay combination. Accordingly, a number of replicates for each analyte/assay combination per chip may be 0.1 (i.e., 1 replicate per 10 chips) to 5, or 1 to 3, or 1 to 2, or preferably 1. A number of replicates for each analyte/assay combination per cartridge may be 0.1 (i.e., 1 replicate per 10 cartridges) to 15, or 1 to 5, or 2 to 4. The number of replicates for each analyte/assay combination per chip and/or cartridge may be defined as a specific value, a maximum number, or a range.

Generally, a control sample is the only analyte in the chamber. When multiple chips are used, having control samples on multiple chips helps to validate the results of that chip. However, not all chips require a control sample. The number of control samples per chip may be 0.25 (i.e., 1 control per 4 chips) to 2, or 0.5 to 1, or more. Relative to cartridges, there may be several controls as the cartridge may contain several chips. Such controls may be all the same control or include a mixture of different controls. The number of control samples per cartridge may be 1 to 20, or 3 to 15, or more.

An amount of chambers in which two or more analyte/assay combinations can be paired may be 1% to 99%, or 10% to 99%, or 50% to 99%, or 75% to 99%. Preferably, more chambers include two or more analyte/assay combinations to maximize the number of analyte/assay combinations tested. Accordingly, the amount of chambers in which two or more analyte/assay combinations can be paired may be 50% to 99%, or 75% to 99%.

A number of analyte/assay combinations per chamber may be 1 to 5, or 3 to 5, or 3 to 4. The number of analyte/assay combinations per chamber may be defined as a specific value, a maximum number, or a range. As described further herein, the number of analyte/assay combinations in an individual chamber depends on the analyte/assay combinations and the potential interaction between the analytes.

Referring again to FIG. 2, the prioritization of a set of analyte/assay combinations 3 ranks the analyte/assay combinations in the set of analyte/assay combinations so that the plurality of candidate panel layouts and, consequently, the one or more panel layout solutions are focused on the analyte/assay combinations that are the most relevant. By incorporating this prioritization aspect into the approach of the present disclosure, the first model 7 does not have to consider all possible candidate panel layouts and can ignore the vast majority of random layouts. This further uniquely improves the efficiency and computing power needed to run the first model.

Prioritizing the set of analyte/assay combinations considers the characteristics of each analyte in the set of analyte/assay combinations. Such characteristics include, but are not limited to, a prevalence of each analyte ($\tau$), a clinical relevance of each analyte ($\theta$), a clinical actionability of each analyte ($\alpha$), a patient benefit ($\beta$), a cost savings ($\delta$), and the like, and any combination thereof.

The characteristics are used in the first model as weights in an algorithm to score each analyte/assay combination, which is the basis of the prioritization rankings. Such weighting and scoring can be performed in a variety of ways. In a nonlimiting example, each characteristic can be attributed a value (e.g., a value of −1 to 1, a value of 0 to 10, or the like) and a summation of the values for each characteristic considered is used to rank the analyte/assay combinations. More complex algorithms can also be used. Each of the characteristics can have a different range of values from which the ranking is based.

The prevalence of each analyte ($\tau$) relates to proportion of the human population that harbors the disease or other biological state associated with the analyte.

The clinical relevance of each analyte ($\theta$) relates to the clinical significativity for the disease or other biological state associated with the analyte. For instance, some bacterial species are not part of the normal human flora and their presence is a clear signature of an infection.

The clinical actionability of each analyte ($\alpha$) relates to the current ability to implement a treatment for the disease or other biological state associated with the analyte.

The patient benefit ($\beta$) relates to the severity of the disease or other biological state associated with the analyte and the degree of benefit to the patient condition.

The cost savings ($\delta$) relates to the healthcare costs spent diagnosing and treating the disease or other biological state associated with the analyte.

The values for each of these characteristics can be determined quantitatively based on databases having data relevant to the characteristic of interest. Where such databases are not available, the values of each of the characteristics can be determined qualitatively based on general knowledge of the characteristic of interest.

Further, each of the characteristics can be, and typically are, geographically dependent. For example, the presence of vanA and/or vanB in bacteria indicates a resistance of the bacteria to the antibiotic vancomycin. vanA and vanB bacteria may be more prevalent in different countries, different cities within a country, or different hospitals within a given area. In another example, healthcare costs are geographically dependent. Accordingly, the approach described herein can be applied to a global analysis, regional analysis, or another subset analysis.

Referring again to FIG. 2, an analyte/analyte interactivity 5 relates to whether or not one analyte/assay combination should be paired with another analyte/assay combination. For example, analytes that cross-react should not be placed in the same chamber (e.g. PCR oligonucleotides producing primer dimers). Alternatively, analytes that do not react or analytes with a convergent clinical relevance should be placed in the same chamber. For example, the presence of vanA or vanB indicates that a bacteria is resistant to vancomycin. Accordingly, a positive interaction between either analyte indicates the assay is resistant to vancomycin.

Like the characteristics of each analyte in the set of analyte/assay combinations, the analyte/analyte interactivity 5 can be attributed a value (e.g., a value of −1 to 1, a value of 0 to 10, or the like).

The first model 7 considers all of the inputs (e.g., the panel layout rules 1, the prioritization of the set of analyte/assay combinations 3, and the analyte/analyte interactivity 5) and produces the plurality of candidate profile layouts 9. Again, because the inputs 1, 2, 3 provide rules and quantitative values by which the candidate profile layouts 9 are developed, not all possible candidate profile layouts 9 need to be considered.

The second model 11 validates the plurality of candidate panel layouts 9 to arrive at one or more panel layout solutions 21 that mitigate ambiguous results. That is, an in silico evaluation predicts the performance of the candidate panel layouts 9 by assessing the potential error in the layout. This is achieved by the second model 11 incorporating a logical chamber allocation analysis 13, a biological feasible challenge analysis 15, a full chamber allocation analysis 17, and an automated testing for the complex analysis 19. Each analyses 13, 15, 17, 19 in a single candidate panel layout 9 may have different potential error. The second model 11 takes into consideration the contribution to total potential error from each of the analyses 13, 15, 17, 19 in to provide one or more panel layout solutions 21 that mitigate ambiguous results.

The logical chamber allocation analysis 13 selects a preferred number of replicates per analyte. Here, the cartridges and device in which the panel is being analyzed is considered. More specifically, the probability of the chamber functioning properly, and the probability of a false negative result are considered.

The biological feasibility challenge generator 15 considers the characteristics (or a subset thereof) of each analyte in the set of analyte/assay combinations described above. More specifically, the probabilities of the chamber providing accurate results, in light of the characteristics (or a subset thereof) of each analyte in the set of analyte/assay combinations, are considered.

The full chamber allocation analysis 17 considers the assay and detection method. More specifically, the probabilities of the chamber providing accurate results, in light of the combination of the assay and detection method, are considered. For example, full chamber allocation analysis considers the mitigation of providing false positives for a specific combination of an assay and a specific detection method, which may include the detection requirements of the assay and the detection limits (e.g., sensitivity at specific wavelengths) of the instruments in detection method.

The automated testing for the complex analysis 19 considers the test harness, which accounts for the potential error in the other analyses and, optionally, may also consider the runtime of the test. The runtime of the test includes the number of chips for a given candidate panel layout 9 and the detection method. The result of the automated testing for the complex analysis 19 is one or more panel layout solutions 21.

The second model 11 may produce one or more panel layout solutions 21 with an indication (e.g., a score or a text description) of the predicted performance of the panel layout solution. For example, two panel layout solutions may have similar performance in general but one panel layout solution may have less ambiguity in the potential performance of a specific analyte/assay combination as compared to another panel layout solution. Then, a user may choose from the one or more panel layout solutions 21 for carrying out a panel experiment.

The methods described herein for identifying candidate panel layouts and/or panel layout solutions can be performed with a system. For example, a system can include a computer system that comprises: a processor; and a tangible, machine-readable storage medium that stores machine-readable instructions for execution by the processor, the machine-readable instructions corresponding to one or more of the methods described herein. That is, the methods described herein can be performed on computing devices (or processor-based devices) that include a processor; a memory coupled to the processor; and instructions provided to the memory, wherein the instructions are executable by the processor to perform the methods (or steps of the methods) described herein. The instructions can be a portion of code on a non-transitory computer readable medium. Any suitable processor-based device may be utilized for implementing all or a portion of embodiments of the present techniques, including without limitation, personal computers, networks personal computers, laptop computers, computer workstations, mobile devices, multi-processor servers or workstations with (or without) shared memory, high performance computers, and the like (and more generally, any physical or virtual processing unit(s) such as a core or a multi-core virtual machine). Moreover, embodiments may be implemented on application specific integrated circuits (ASICs) or very large scale integrated (VLSI) circuits.

The terms "non-transitory, computer-readable medium," "tangible machine-readable medium," or the like refer to any tangible storage that participates in providing instructions to a processor for execution. Such a medium may take many forms, including but not limited to, non-volatile media and volatile media. Non-volatile media includes, for example, NVRAM, or magnetic or optical disks. Volatile media includes dynamic memory, such as main memory. Computer-readable media may include, for example, a floppy disk, a flexible disk, hard disk, magnetic tape, or any other magnetic medium, magneto-optical medium, a CD-ROM, any other optical medium, a RAM, a PROM, and EPROM, a FLASH-EPROM, a solid state medium like a holographic memory, a memory card, or any other memory chip or cartridge, or any other physical medium from which a computer can read. When the computer-readable media is configured as a database, it is to be understood that the database may be any type of database, such as relational, hierarchical, object-oriented, and/or the like. Accordingly, exemplary embodiments of the present techniques may be considered to include a tangible storage medium or tangible distribution medium and prior art-recognized equivalents and successor media, in which the software implementations embodying the present techniques are stored.

The methods and systems described herein may be applied to design a variety of in vitro diagnostic systems including, but not limited to, amplification technologies (e.g., PCR, LAMP, RPA, RCA, and the like), sequencing technologies (e.g., DNA and RNA sequencing, nucleic acid modifications sequencing (e.g., methylated bases sequencing and protein sequencing using ISFET)), hybridizing (e.g., described in WO/2015/0162301, incorporated herein by reference), and the like. Accordingly, methods described herein may further include (a) testing the analyte/assay combinations per at least one of the one or more panel layout solutions and (b) amplifying and/or sequencing and/or hybridizing the analyte in at least one of the chambers, preferably the analytes that provide positive results.

ISFETs and other chemical FETs (ChemFETs) may be a preferred system for the foregoing methods. The use of ISFETs to sequence DNA and DNA fragments (as well as RNA and RNA fragments) is described for example in WO/2003/073088, incorporated herein by reference. This work has demonstrated that the incorporation of nucleotides (A,T,C,G) during extension of a DNA strand can be monitored by using an ISFET to measure the variation in ionic concentration as a by-product of the reaction. When a nucleotide extends a DNA strand, it releases pyrophosphate which is hydrolyzed and generates H+ ions, reducing the pH. In a similar way, an ISFET can be used to detect hybridization, whereby a hybridization probe attaches to a matching sequence on a DNA strand. An extension of this approach using very large scale FET arrays is described in US2009/0026082, incorporated herein by reference, and provides for massively parallel analysis. By analyzing a large number of DNA fragments in parallel, and then aligning and "stitching" together the results, long sections of DNA may be sequenced in a relatively short time. In the case of an ISFET based assay, the ISFET chip will be designed and manufactured to perform one or a set of predefined assays. For example, The ISFET chip will be configured to detect the presence of a set of single nucleotide polymorphisms (SNPs) in a sequence of DNA. The sample is first prepared on the laboratory bench. This may involve enriching the sample to remove material other than the cells, lysing the enriched cells to release the DNA, and performing amplification on one or more DNA sequences. During or following this process, the amplified DNA sequences are attached to micro beads. These beads are then introduced to the chip. This might involve depositing the beads into wells formed above the individual ISFETs (e.g., using magnetic beads to introduce one bead into each well). The chip can then be inserted into an instrument where the sequencing is performed. The instrument causes different nucleotides (A,T,C,G) to be flowed cyclically through the chip, with a washing step between each nucleotide flow. Electrical signals representing chain extensions are detected. The result provided by the instrument is a chain extension sequence for each ISFET. This data is then analyzed, for example using a desktop PC connected to the analyzer, to weigh the results according to their prevalence. Sequences that have a high prevalence will be recorded as valid sequences, whilst sequences with a relatively low prevalence will be recorded as being due to noise. The valid sequences may then be used to determine the presence or absence of a SNP(s) in the analyzed sample. Of course, other workflows and analysis routines are possible. In addition to these essentially laboratory-bound assay processes, point-of-care assay procedures and systems have been developed. For example, DNA Electronics (London, UK) has developed a genetic testing kit that allows procedures such as that described above to be conducted by essentially unskilled persons at a point-of-care or point-of-sale. In many cases, testing using an ISFET-based assay will form only one part in a workflow that will be followed by a skilled technician. Based on the result of the ISFET-based assay, decisions may need to be made concerning further tests, and these tests will need to be performed (e.g., using further ISFET-based assays).

WO/2011/034790 and US2012/0109531 present exemplary biological and physiological assay schemes and instruments that provide a degree of automation and flexibility and are not directly applicable to the handling of nucleic acids.

EXAMPLE EMBODIMENTS

A first nonlimiting example embodiment of the present disclosure is a method comprising: prioritizing a set of analyte/assay combinations based on characteristics of each analyte in the set of analyte/assay combinations, wherein the characteristics comprise one selected from the group consisting of a prevalence of each analyte, a clinical relevance of each analyte, a clinical actionability of each analyte, a patient benefit, a cost savings, and any combination thereof; deriving an analyte/analyte interactivity for two or more analytes in the set of analyte/assay combinations; and designing a plurality of candidate panel layouts based on panel layout rules, the prioritization of the set of analyte/assay combinations, and the analyte/analyte interactivity, wherein the panel layout comprises one or more chips each comprising a chamber with two or more analytes; and validating the plurality of candidate panel layouts to produce one or more panel layout solutions. Said example embodiment may further include one or more of: Element 1: wherein the one or more chips comprise ion sensitive field effect transistor chips; Element 2: wherein the panel layout rules comprise a rule selected from the group consisting of a number of replicates for each analyte/assay combination in the panel, a number of replicates for each analyte/assay combination per chip, a number of control chambers, a number of control chambers per chip, an amount of chambers in which two or more analyte/assay combinations are paired, a number of analyte/assay combinations per chamber, and any combination thereof; Element 3: Element 2 and wherein the number of replicates for each analyte/assay combination per panel ranges from 2 to 5; Element 4: Element 2 and wherein the number of replicates for each analyte/assay combination per chip ranges from 1 to 5; Element 5: Element 2 and wherein the number of control samples per chip ranges from 0.25 to 2; Element 6: Element 2 and wherein the amount of chambers in which two or more analyte/assay combinations are paired ranges from 10% to 99%; Element 7: Element 2 and wherein the number of analyte/assay combinations per chamber ranges from 1 to 5; Element 8: wherein the characteristics are based on geographic location; Element 9: the method further comprising: testing the analyte/assay combinations per at least one of the one or more panel layout solutions; Element 10: Element 9 and wherein at least 50% of the chambers of the panel layout have two or more analytes; Element 11: Element 9 and the method further comprising: amplifying the analyte in at least one of the chambers; Element 12: Element 9 and the method further comprising: sequencing the analyte in at least one of the chambers; and Element 13: Element 9 and the method further comprising: hybridizing the analyte in at least one of the chambers. Examples of combinations include, but are not limited to, Element 2 in combination with two or more of Elements 3-7; Element 9 in combination with two or more of Elements 10-13; Element 1 and/or Element 8 in combination with Element 2 and optionally in further combination with one or more of Elements 3-7; Element 1 and/or Element 8 in combination with Element 9 and optionally in further combination with one or more of Elements 10-13; Elements 1 and 8 in combination; and Element 2 (optionally in combination with one or more of Elements 3-7) in combination with Element 9 (optionally in combination with one or more of Elements 10-13) and optionally in further combination with Element 1 and/or Element 8.

A second nonlimiting example embodiment of the present disclosure is a system comprising: a processor; a non-transitory machine-readable medium that stores machine-readable instructions for execution by the processor, the machine-readable instructions comprising: prioritize a set of analyte/assay combinations based on characteristics of each analyte in the set of analyte/assay combinations, wherein the characteristics comprise one selected from the group consisting of a prevalence of each analyte, a clinical relevance of each analyte, a clinical actionability of each analyte, a patient benefit, a cost savings, and any combination thereof; derive an analyte/analyte interactivity for two or more analytes in the set of analyte/assay combinations; design a plurality of candidate panel layouts based on panel layout rules, the prioritization of the set of analyte/assay combinations, and the analyte/analyte interactivity, wherein the panel layout comprises one or more chips each comprising a chamber with two or more analytes; and validate the plurality of candidate panel layouts to produce one or more panel layout solutions. Said example embodiment may further include one or more of: Element 1; Element 2; Element 3; Element 4; Element 5; Element 6; Element 7; Element 8; Element 14: the machine-readable instructions further comprising: test the analyte/assay combinations per at least one of the one or more panel layout solutions; Element 15: Element 14 and wherein at least 50% of the chambers of the panel layout have two or more analytes; Element 16: Element 14 and the machine-readable instructions further comprising: amplify the analyte in at least one of the chambers; Element 17: Element 14 and the machine-readable instructions further comprising: sequence the analyte in at least one of the chambers; and Element 18: Element 14 and the machine-readable instructions further comprising: hybridize the analyte in at least one of the chambers. Examples of combinations include, but are not limited to, Element 2 in combination with two or more of Elements 3-7; Element 14 in combination with two or more of Elements 15-18; Element 1 and/or Element 8 in combination with Element 2 and optionally in further combination with one or more of Elements 3-7; Element 1 and/or Element 8 in combination with Element 14 and optionally in further combination with one or more of Elements 15-18; Elements 1 and 8 in combination; and Element 2 (optionally in combination with one or more of Elements 3-7) in combination with Element 14 (optionally in combination with one or more of Elements 15-18) and optionally in further combination with Element 1 and/or Element 8.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating the invention embodiments disclosed herein are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

To facilitate a better understanding of the embodiments of the present invention, the following examples of preferred or representative embodiments are given. In no way should the following examples be read to limit, or to define, the scope of the invention.

EXAMPLES

A panel having four ion-sensitive field-effect transistor (ISFET) chips each with six chambers was modeled. The panel rules included two to three replicates per analyte/assay combination, one positive control on three of the four chips, and a maximum of three analyte/assay combinations per chamber. The control was *Schizosaccharomyces pombe* ("*S. pombe*"). The bacteria and antimicrobial resistant (AMR) gene analytes considered are in Table 1. These analytes were chosen because they are clinically relevant to sepsis. Additional analytes like pgaD were used.

TABLE 1

| Analytes | | | |
|---|---|---|---|
| Bacteria or Fungi | | AMR Genes | Species Specific Genes |
| *Acinetobacter baumannii* | *Escherichia coli* | KPC | uidA |
| *Candida albicans* | *Klebsiella oxytoca* | mecA/mecC | |
| *Candida glabrata* | *Klebsiella pneumoniae* | vanA/vanB | |
| *Candida krusei* | *Pseudomonas aeruginosa* | CTX-M | |
| *Candida tropicalis* | *Staphylococcus aureus* | | |
| *Enterobacter aerogenes* | *Staphylococcus epidermidis* | | |
| *Enterobacter cloacae complex* | *Staphylococcus* spp. | | |
| *Enterococcus faecalis* | *Streptococcus* spp./ *Serratia. marcescens*/ *Proteus mirabilis* | | |
| *Enterococcus faecium* | | | |

The prioritization of a set of analyte/assay combinations was based, at least in part, on Tables 2, 3, and 4, which provide values for the prevalence of an analyte, the relevance of an analyte as a biocontaminant, and the actionability of an analyte, respectively, by a geographic location.

TABLE 2

| | Prevalence (scale of 0 to 1) | | | | | |
|---|---|---|---|---|---|---|
| | mecA | uidA | vanA | vanB | CTX-M | pgaD |
| United Kingdom | 0.3 | 0.3 | 0.1 | 0.1 | 0.1 | 0.1 |
| United States | 0.3 | 0.3 | 0.1 | 0.1 | 0.1 | 0.1 |
| China | 0.3 | 0.2 | 0.01 | 0.01 | 0.2 | 0.2 |
| New York | 0.3 | 0.3 | 0.1 | 0.1 | 0.1 | 0.1 |
| Royal Free Hospital, London | 0.3 | 0.3 | 0.01 | 0.01 | 0.2 | 0.1 |
| Mt. Sinai Hospital, New York | 0.3 | 0.3 | 0.1 | 0.1 | 0.1 | 0.1 |

TABLE 3

| | Relevance (scale of 0 to 1) | | | | | |
|---|---|---|---|---|---|---|
| | P. aeruginosa | S. epidermidis | E. coli | mecA | mecC | P. mirabdis |
| United Kingdom | 0.01 | 0.3 | 0.4 | 0.1 | 0.1 | 0.01 |
| United States | 0.1 | 0.2 | 0.4 | 0.1 | 0.1 | 0.1 |
| China | 0.01 | 0.2 | 0.3 | 0.01 | 0.2 | 0.2 |
| New York | 0.1 | 0.2 | 0.4 | 0.1 | 0.1 | 0.1 |
| Royal Free Hospital, London | 0.1 | 0.2 | 0.4 | 0.01 | 0.2 | 0.2 |
| Mt. Sinai Hospital, New York | 0.01 | 0.3 | 0.4 | 0.1 | 0.1 | 0.01 |

TABLE 4

| | Actionability (scale of 0 to 1) | | | | | |
|---|---|---|---|---|---|---|
| | P. aeruginosa | S. epidermidis | E. coli | mecA | mecC | P. mirabdis |
| United Kingdom | 0.01 | 0.3 | 0.4 | 0.4 | 0.3 | 0.01 |
| United States | 0.01 | 0.3 | 0.4 | 0.4 | 0.3 | 0.01 |
| China | 0.1 | 0.2 | 0.5 | 0.01 | 0.01 | 0.1 |
| New York | 0.01 | 0.3 | 0.4 | 0.4 | 0.3 | 0.01 |
| Royal Free Hospital, London | 0.01 | 0.3 | 0.4 | 0.4 | 0.3 | 0.01 |
| Mt. Sinai Hospital, New York | 0.01 | 0.3 | 0.4 | 0.4 | 0.3 | 0.01 |

Figure 3:
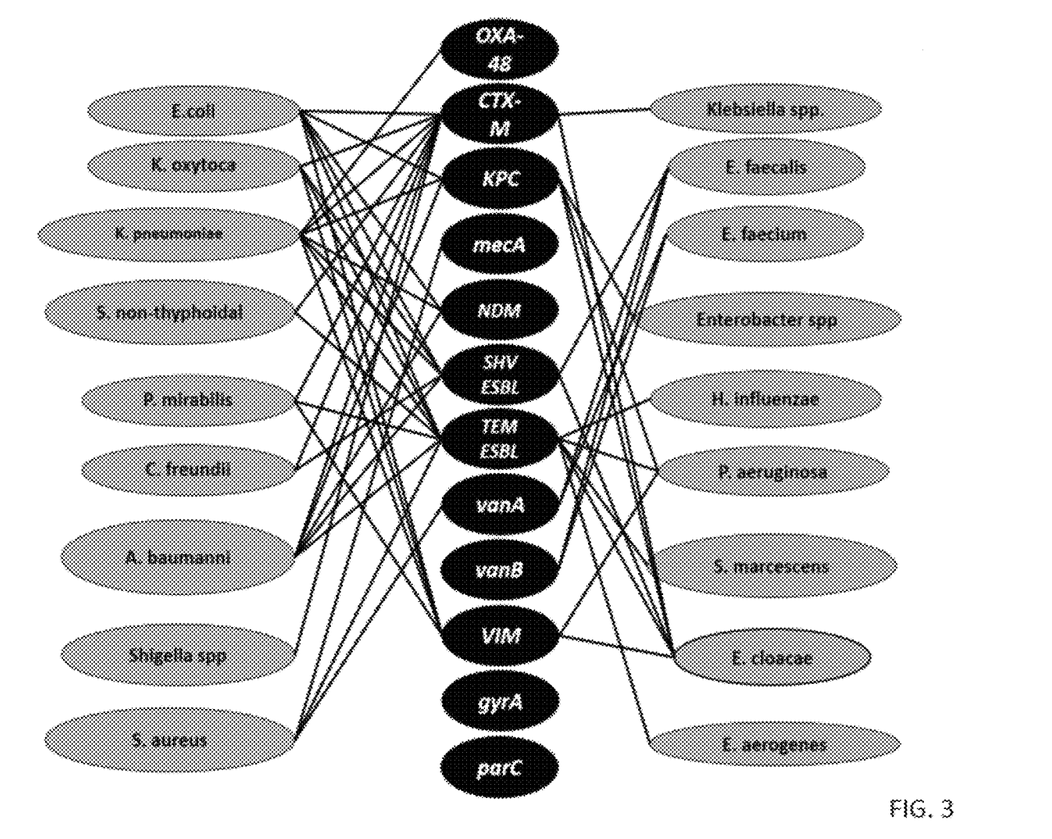
FIG. 3 illustrates the links between the antimicrobial resistant (AMR) genes and the species of bacteria.

FIG. 3 illustrates the links between the AMR genes and the species of bacteria. This provides at least a portion of the basis for the analyte/analyte interactivity. The bacteria in FIG. 3 are linked to AMR genes present in said bacteria, so having both in the same chamber would be less desirable. More specifically, the analyte/analyte interactivity was based, at least in part, on Tables 5 and 6, which provide values for a grouping matrix and a compatibility matrix, respectively. The grouping matrix is based on FIG. 3 where lower values indicate analytes that should not be placed together because the AMR gene is present in the bacteria species. The compatibility matrix relates to reactivity of the analytes where lower values indicate higher reactivity.

TABLE 5

| | Grouping (scale of −1 to 1) | | | | | |
|---|---|---|---|---|---|---|
| | S. aureus | E. faecium | mecA | Positive Control | vanA | vanB |
| S. aureus | −1 | 0 | −1 | −1 | 0 | 0 |
| E. faecium | 0 | −1 | 0 | −1 | 0 | 0 |
| mecA | −1 | 0 | −1 | −1 | 0 | 0 |

TABLE 5-continued

| | Grouping (scale of −1 to 1) | | | | | |
|---|---|---|---|---|---|---|
| | S. aureus | E. faecium | mecA | Positive Control | vanA | vanB |
| Positive Control | −1 | −1 | −1 | −1 | −1 | −1 |
| vanA | 0 | −1 | 0 | −1 | −1 | 1 |
| vanB | 0 | −1 | 0 | −1 | 1 | −1 |

TABLE 6

| | Reactivity (scale of −1 to 1) | | | | | |
|---|---|---|---|---|---|---|
| | S. aureus | P. aeruginosa | mecA | K. pneumonia | K. oxy. Amp. 01 | K. oxy. Amp. 02 |
| S. aureus | −1 | 0 | 0 | 0 | 0 | 0 |
| P. aeruginosa | 0 | −1 | −1 | 0 | −1 | 0 |
| mecA | 0 | 0 | −1 | 0 | 0 | 0 |
| K. pneumoniae | 0 | 0 | 0 | −1 | 0 | 0 |
| K. oxy. Amp. 01 | 0 | 0 | 0 | 0 | −1 | 1 |
| K. oxy. Amp. 02 | 0 | 0 | 0 | 0 | 1 | −1 |

Three candidate panel layouts for the four chips using the United States regional inputs are provided in Tables 7-9 where the number in parentheses after the analyte is the replicate number. Tables 7 and 8 are based on a subset of the analytes from Table 1. The subset of analytes was chosen based on the prioritization of a set of analyte/assay combinations. Tables 7 and 8 include two to three replicates per analyte, where Table 8 has three more replicate analytes than Table 8. Table 9 includes three replicates per analyte.

TABLE 7

Candidate Panel Layout 1

Chip A *no positive control*

| Chamber 1 | Chamber 2 | Chamber 3 |
|---|---|---|
| vanA/vanB (1) | mecA/mecC (1) | KPC (1) |

| Chamber 4 | Chamber 5 | Chamber 6 |
|---|---|---|
| E. coli (1) | E. faecium (1) | S. aureus (1) |

Chip B

| Chamber 1 | Chamber 2 | Chamber 3 |
|---|---|---|
| vanA/vanB (2) | K. pneumonia (1) | A. baumannii (1) |

| Chamber 4 | Chamber 5 | Chamber 6 |
|---|---|---|
| P. aeruginosa (1) | E. cloacae complex (1) | S. pombe (1) |

Chip C

| Chamber 1 | Chamber 2 | Chamber 3 |
|---|---|---|
| mecA/mecC (2) | E. coli (2) | E. faecium (2) |

| Chamber 4 | Chamber 5 | Chamber 6 |
|---|---|---|
| S. aureus (2) | K. pneumonia (2) | A. baumannii (2) |

Chip D

| Chamber 1 | Chamber 2 | Chamber 3 |
|---|---|---|
| KPC (2) | P. aeruginosa (2) | mecA/mecC (3) |

| Chamber 4 | Chamber 5 | Chamber 6 |
|---|---|---|
| E. cloacae complex (2) | S. pombe (2) | vanA/vanB (3) |

TABLE 8

Candidate Panel Layout 2

Chip A *no positive control*

| Chamber 1 | Chamber 2 | Chamber 3 |
|---|---|---|
| vanA/vanB (1) | mecA/mecC (1) | KPC (1) |

| Chamber 4 | Chamber 5 | Chamber 6 |
|---|---|---|
| E. coli (1) | E. faecium (1) | S. aureus (1) |
| E. cloacae complex (1) | A. baumannii (1) | |

Chip B

| Chamber 1 | Chamber 2 | Chamber 3 |
|---|---|---|
| vanA/vanB (2) | K. pneumoniae (1) | A. baumannii (2) |
| S. aureus (2) | | E. coli (2) |

| Chamber 4 | Chamber 5 | Chamber 6 |
|---|---|---|
| P. aeruginosa (1) | E. cloacae complex (2) | S. pombe (1) |
| | P. aeruginosa (2) | |

TABLE 8-continued

Candidate Panel Layout 2

Chip C

| Chamber 1 | Chamber 2 | Chamber 3 |
|---|---|---|
| mecA/mecC (2) | E. coli (3) | E. faecium (2) |

| Chamber 4 | Chamber 5 | Chamber 6 |
|---|---|---|
| S. aureus (3) | K. pneumoniae (2) | A. baumannii (3) |
| KPC (2) | | |

Chip D

| Chamber 1 | Chamber 2 | Chamber 3 |
|---|---|---|
| KPC (2) | P. aeruginosa (3) | mecA/mecC (3) |
| | | E. faecium (3) |

| Chamber 4 | Chamber 5 | Chamber 6 |
|---|---|---|
| E. cloacae complex (3) | S. pombe (2) | vanA/vanB (3) |

TABLE 9

Candidate Panel Layout 3

Chip A *no positive control*

| Chamber 1 | Chamber 2 | Chamber 3 |
|---|---|---|
| K. oxytoca (2) | mecA/mecC (2) | S. aureus (3) |
| C. glabrata (1) | K. oxytoca (3) | A. baumannii (2) |
| E. faecalis (1) | Strep spp./S. marcescens/ P. mirabilis (1) | E. aergenes (1) |

| Chamber 4 | Chamber 5 | Chamber 6 |
|---|---|---|
| S. epidermidis (2) | vanA/vanB (1) | E. faecium (2) |
| E. cloacae complex (3) | C. krusei (3) | K. pneumoniae (1) |
| C. albicans (3) | P. aeruginosa (3) | Staph. spp. (1) |

Chip B

| Chamber 1 | Chamber 2 | Chamber 3 |
|---|---|---|
| S. pombe (2) | mecA/mecC (1) | E. faecalis (3) |
| | P. aeruginosa (2) | E. coli (3) |
| | K. pneumoniae (3) | Strep spp./ S. marcescens/ P. mirabilis (2) |

| Chamber 4 | Chamber 5 | Chamber 6 |
|---|---|---|
| S. epidermidis (1) | vanA/vanB (3) | E. faecium (1) |
| K. oxytoca (1) | E. cloacae complex (2) | KPC (3) |
| C. tropicalis (2) | C. glabrata (3) | E. aergenes (2) |

Chip C

| Chamber 1 | Chamber 2 | Chamber 3 |
|---|---|---|
| S. pombe (1) | mecA/mecC (3) | S. aureus (2) |
| | A. baumannii (3) | P. aeruginosa (1) |
| | C. albicans (1) | C. krusei (1) |

| Chamber 4 | Chamber 5 | Chamber 6 |
|---|---|---|
| S. epidermidis (3) | C. tropicalis (3) | KPC (2) |
| E. coli (1) | Staph. spp. (3) | E. faecium (3) |
| vanA/vanB (2) | | C. glabrata (2) |

TABLE 9-continued

Candidate Panel Layout 3

Chip D

| Chamber 1 | Chamber 2 | Chamber 3 |
|---|---|---|
| S. pombe (3) | E. faecalis (2)<br>C. albicans (2)<br>E. cloacae complex (1) | KPC (1)<br>C. krusei (2) |

| Chamber 4 | Chamber 5 | Chamber 6 |
|---|---|---|
| E. coli (2)<br>E. aergenes (3)<br>C. tropicalis (1) | K. pneumoniae (2)<br>S. aureus (1)<br>Strep spp./S. marcescens/<br>P. mirabilis (3) | A. baumannii (1)<br>Staph. spp. (2) |

Then, a second model was used to validate the candidate panel layouts to produce a panel layout solution. The chips and device used in this example have a high probability of the chamber functioning properly and a low probability of a false negative result.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces.

The invention claimed is:

1. A method of selecting a panel layout solution for a cartridge for use in an in vitro diagnostic system for identifying a plurality of analytes in a sample, the cartridge comprising an array of chambers overlaying one or more chips each of said chambers being configured to contain at least one analyte, said in vitro diagnostic system being configured to perform a plurality of assays, said method comprising:

prioritizing analyte assay combinations within a set of analyte assay combinations based on characteristics of each analyte in the set of analyte assay combinations, wherein the characteristics comprise at least one selected from the group consisting of a prevalence of each analyte, a clinical relevance of each analyte, a clinical actionability of each analyte, a patient benefit, and a cost saving;

deriving an interactivity between analytes for two or more analytes in the set of analyte assay combinations; and designing a plurality of candidate panel layouts based on panel layout rules, the prioritization of the set of analyte assay combinations, and the interactivity between analytes, wherein the plurality of candidate panel layouts each comprise one or more chips each overlaid by a plurality of chambers, wherein one or more of the plurality of chambers for at least one of the one or more chips is assigned two or more analyte assay combinations per chamber to be performed in said in vitro diagnostic system;

validating the plurality of candidate panel layouts to produce one or more panel layout solutions; and selecting from the one or more panel layout solutions based on the validation.

2. The method of claim 1, wherein the one or more chips comprise ion sensitive field effect transistor chips.

3. The method claim 1, wherein the panel layout rules comprise a rule selected from the group consisting of a number of replicates for each analyte assay combination in the panel, a number of replicates for each analyte assay combination per chip, a number of control chambers, a number of control chambers per chip, a number of chambers in which the two or more analyte assay combinations are paired, a number of analyte assay combinations per chamber, and any combination thereof.

4. The method of claim 3, wherein the number of replicates for each analyte assay combination per panel ranges from 2 to 5.

5. The method of claim 3, wherein the number of replicates for each analyte assay combination per chip ranges from 1 to 5.

6. The method of claim 3, wherein the number of control samples per chip ranges from 0.25 to 2.

7. The method of claim 3, wherein the number of chambers in which the two or more analyte assay combinations are paired ranges from 10% to 99%.

8. The method of claim 3, wherein the number of analyte assay combinations per chamber ranges from 1 to 5.

9. The method of claim 1, wherein the characteristics are based on geographic location.

10. The method of claim 1 further comprising:

testing the analyte assay combinations according to at least one of the one or more panel layout solutions.

11. The method of claim 10, wherein at least 50% of the chambers of the panel layout have two or more analytes.

12. The method of claim 10 further comprising:

amplifying the analyte in at least one of the chambers.

13. The method of claim 10 further comprising:

sequencing the analyte in at least one of the chambers.

14. The method of claim 10 further comprising:

hybridizing the analyte in at least one of the chambers.

15. The method of claim 1 further comprising:

preparing said cartridge by filling each of said plurality of chambers with said analytes according to said selected panel layout solution.

16. A system comprising:

a processor;

a non-transitory machine-readable medium that stores machine-readable instructions for execution by the processor, the machine-readable instructions comprising:

prioritize analyte assay combinations within a set of analyte assay combinations based on characteristics of each analyte in the set of analyte assay combinations, wherein the characteristics comprise at least one selected from the group consisting of a prevalence of each analyte, a clinical relevance of each analyte, a clinical actionability of each analyte, a patient benefit, and a cost saving;

derive an interactivity between analytes for two or more analytes in the set of analyte assay combinations;

design a plurality of candidate panel layouts based on panel layout rules, the prioritization of the set of analyte assay combinations, and the interactivity between analytes, wherein the plurality of candidate panel layouts each comprise one or more chips each overlaid by a plurality of chambers, wherein one or more of the plurality of chambers for at least one of the one or more chips is assigned two or more analyte assay combinations per chamber to be performed in an in vitro diagnostic system; and validate the plurality of candidate panel layouts; and produce one or more panel layout solutions based on the validation.

17. The system of claim 16, wherein the panel layout rules comprise a rule selected from the group consisting of a number of replicates for each analyte assay combination in the panel, a number of replicates for each analyte assay combination per chip, a number of control chambers, a number of control chambers per chip, a number of chambers in which the two or more analyte assay combinations are paired, a number of analyte assay combinations per chamber, and any combination thereof.

18. The system of claim 16, wherein the number of replicates for each analyte assay combination per panel ranges from 2 to 5.

19. The system of claim 17, wherein the number of replicates for each analyte assay combination per chip ranges from 1 to 5.

20. The system of claim 17, wherein the number of control samples per chip ranges from 0.25 to 2.

21. The system of claim 17, wherein the number of chambers in which the two or more analyte assay combinations are paired ranges from 10% to 99%.

22. The system of claim 17, wherein the number of analyte assay combinations per chamber ranges from 1 to 5.

23. The method of claim 16, wherein the machine-readable instructions further comprise:

test at least one of the one or more panel layout solutions in the in vitro diagnostic system.

* * * * *